(12) United States Patent
Nakao

(10) Patent No.: US 7,122,003 B2
(45) Date of Patent: Oct. 17, 2006

(54) ENDOSCOPIC RETRACTOR INSTRUMENT AND ASSOCIATED METHOD

(75) Inventor: Naomi L. Nakao, New York, NY (US)

(73) Assignee: Granit Medical Innovations, LLC, New York, NY (US)

( * ) Notice: Subject to any disclaimer, the term of this patent is extended or adjusted under 35 U.S.C. 154(b) by 167 days.

(21) Appl. No.: 10/414,749

(22) Filed: Apr. 16, 2003

(65) Prior Publication Data

US 2004/0210116 A1    Oct. 21, 2004

(51) Int. Cl.
*A61B 1/32* (2006.01)
*A61M 29/00* (2006.01)

(52) U.S. Cl. .................................. 600/204; 606/198

(58) Field of Classification Search ............... 600/205, 600/121, 204, 207; 606/192, 198, 191; 604/101.02
See application file for complete search history.

(56) References Cited

U.S. PATENT DOCUMENTS

| | | | | |
|---|---|---|---|---|
| 4,183,102 A * | 1/1980 | Guiset | .................. | 623/1.25 |
| 4,984,564 A * | 1/1991 | Yuen | .................. | 600/207 |
| 5,649,978 A * | 7/1997 | Samson | .................. | 606/198 |
| 5,743,851 A * | 4/1998 | Moll et al. | .................. | 600/204 |
| 6,146,401 A | 11/2000 | Yoon et al. | | |
| 6,179,854 B1 | 1/2001 | Nash et al. | | |
| 6,409,723 B1 * | 6/2002 | Edwards | .................. | 606/41 |
| 6,605,037 B1 * | 8/2003 | Moll et al. | .................. | 600/204 |
| 2003/0225433 A1 * | 12/2003 | Nakao | .................. | 606/191 |

\* cited by examiner

*Primary Examiner*—Pedro Philogene
(74) *Attorney, Agent, or Firm*—R. Neil Sudol; Henry D. Coleman; William J. Sapone

(57) ABSTRACT

An endoscopic retractor instrument assembly includes a balloon having a pair of expandable or inflatable end portions and at least one expandable or inflatable spacer portion connecting the end portions to one another. A fastener is provided for securing the balloon to a distal end of an endoscopic insertion member, with the balloon being disposed in a collapsed configuration along an outer surface of the endoscopic insertion member. An inflation element is operatively coupled with the balloon for enabling an inflating of the balloon from the collapsed configuration to an expanded use configuration in which the spacer portion pushes the end portions apart from one another and in which the balloon extends at least partially in a distal direction away from the distal end of the endoscopic insertion member for spreading internal tissues of a patient to facilitate access to the tissues via the endoscopic insertion member.

27 Claims, 13 Drawing Sheets

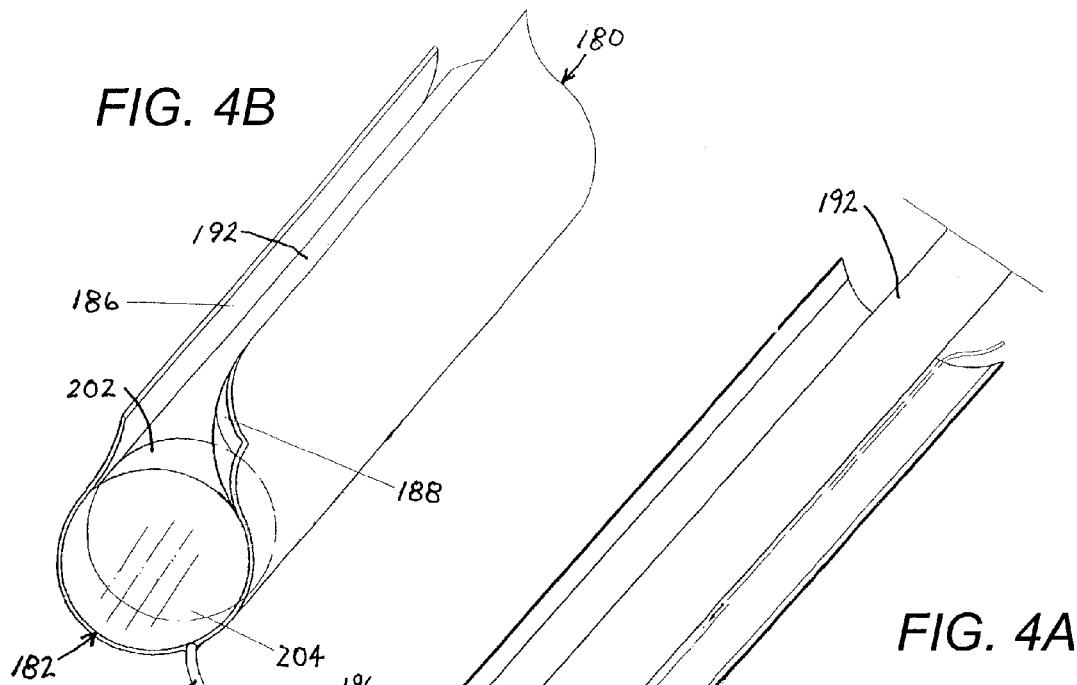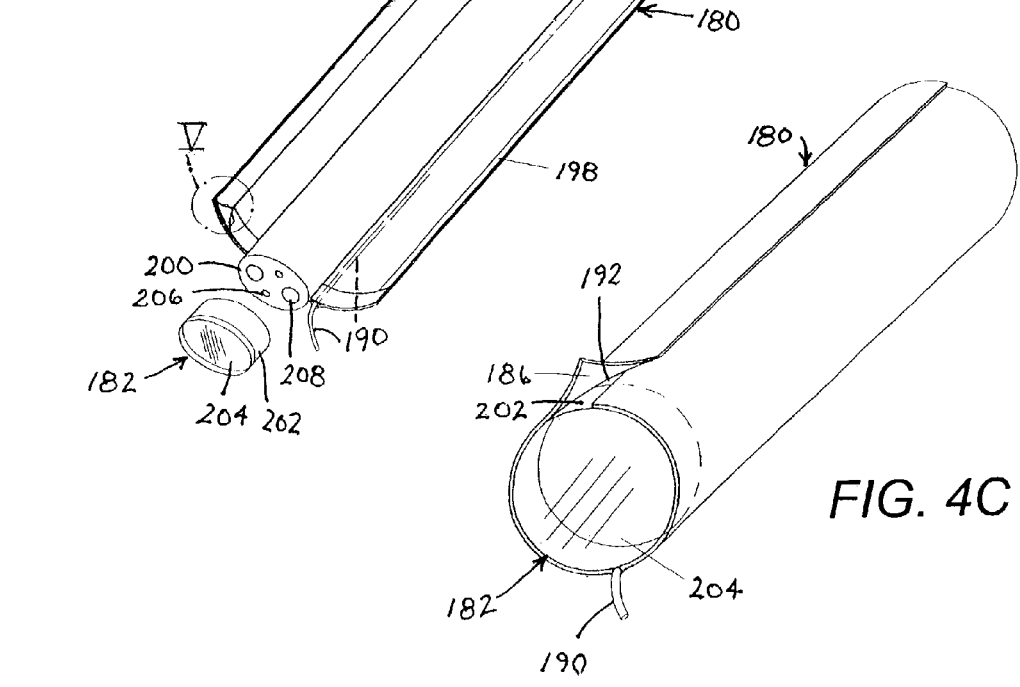

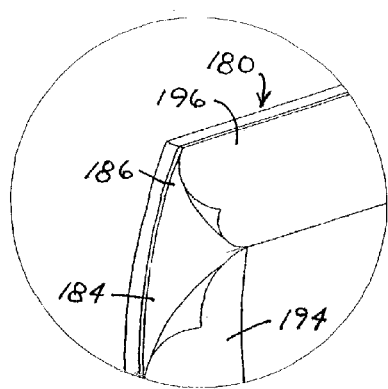
FIG. 5
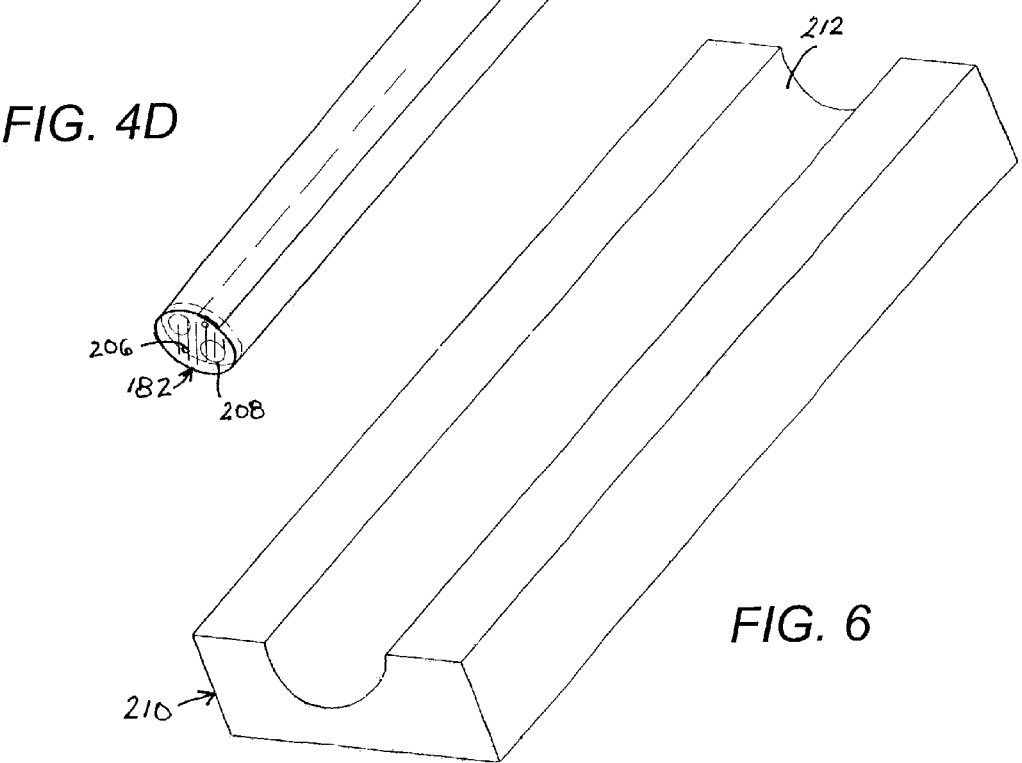
FIG. 4D
FIG. 6

ENDOSCOPIC RETRACTOR INSTRUMENT AND ASSOCIATED METHOD

BACKGROUND OF THE INVENTION

This invention relates to a medical device and to an associated medical technique. More particularly, this invention relates to an endoscopic instrument and to an endoscopic method.

Flexible endoscopes are inserted into the digestive tract for diagnostic and therapeutic purposes. Endoscopes generally include a light guide for transmitting optical-wavelength electromagnetic radiation into the patient. Images are captured, typically via lenses and an optical fiber bundle or a charge-coupled device, whereby a user can visually inspect the inner walls or surfaces of the digestive tract. One common objective of endoscopic investigations in the digestive tract is to detect the presence of polyps. Where a polyp is visually detected, particularly in the colon, it should be severed, captured, and removed from the patient. Alternatively, particularly where the polyp may be a malignant cancer, the polyp may be severed and captured for extraction from the patient.

One problem frequently encountered by endoscopists is that folds of tissues in the digestive tract and particularly the colon can obscure polyps so that they can be overlooked. The colon is often collapsed and may be partially or completely draped over a lesion. In order to distend the walls of the colon, the endoscopist often pumps air into the organ. However, if too much air is introduced, the colon could perforate. Also, the patient is made quite uncomfortable with introduction of substantial amounts of air.

Another problem with visualization during an endoscopic procedure is that polyps sometimes bleed when they are severed. If the lesion site cannot be adequately visualized, it is difficult to contain and control the bleeding.

Further problems in performing endoscopy include the time it takes to reprocess the endoscope between procedures, the potential for transmission of infection from one patient to another because of remaining bioburden inside or on the endoscope, and the added cost to the endoscopy units because of the time spent in manual cleaning of the endoscopes.

OBJECTS OF THE INVENTION

It is a general object of the present invention to provide a retractor instrument utilizable in surgical and/or diagnostic procedures.

A more specific object of the present invention is to provide such an instrument assembly which is utilizable in endoscopic procedures.

A further object of the present invention is to provide such an instrument assembly which is inexpensive and/or easy to use.

It is an even more specific object of the present invention to provide an endoscopic instrument assembly which is particularly suitable for use with flexible endoscopes during investigations of the digestive or gastro-intestinal tract or other internal body cavities.

It is another object of the present invention to provide an endoscopic procedure for facilitating visual inspection of the digestive tract.

An additional object of the present invention is to provide an instrument and/or method for use with flexible endoscopes, which reduces patient discomfort and risk by potentially reducing the amount of air introduced into the gastrointestinal tract.

A further objective is to minimize the amount of time it takes to reprocess an endoscope between successive procedures.

Another objective is to avoid transmission of infection from one procedure to the next owing to the convoluted and intricate shape of the endoscope that allows bioburden to remain lodged in or on the endoscope.

It is yet another object of the present invention to provide an endoscopic instrument that is disposable.

These and other objects of the invention will be apparent from the drawings and descriptions herein. Although every object of the invention is attained by at least one embodiment of the invention, there is not necessarily any one embodiment that achieves all of the objects of the invention.

SUMMARY OF THE INVENTION

An endoscopic retractor instrument assembly comprises, in accordance with the present invention, a balloon having at least one expandable or inflatable end portion and at least one expandable or inflatable spacer portion connected to the end portion. A fastener component is provided for securing the balloon to a distal end of an endoscopic insertion member, with the balloon being disposed in a collapsed configuration along an outer surface of the endoscopic insertion member. An inflation element is operatively coupled with the balloon for enabling an inflating of the balloon from the collapsed configuration to an expanded use configuration in which the spacer portion pushes the end portion in a distal direction away from the distal end of the endoscopic insertion member for spreading internal tissues of a patient to facilitate access to the tissues via the endoscopic insertion member.

Pursuant to another feature of the present invention, the balloon is a unitary single-piece balloon preformed so that the expanded configuration includes the end portion and the spacer portion. The balloon is preferably formed from an elongate tubular preform by bending and winding the preform to form the balloon so that the balloon has a singular flow path for the introduction of a pressurizing fluid.

The fastener may include a sheath disposable about the endoscopic insertion member and/or an end cap attached over a distal tip of the endoscopic insertion member. Preferably, the sheath includes at least one adhesive strip for detachably securing the sheath to the insertion member. The sheath preferably includes a tear string for severing the sheath to facilitate removal thereof from the insertion member. The tear string is preferably disposed along a weakened area of the sheath to facilitate the severing of the sheath and the separation of the tear string from the sheath The end portion of the balloon may take the form of a coil. At an end opposite the coil, the balloon may include an end portion in the form of a coil or a C-shaped segment.

A medical method comprises, in accordance with the present invention, providing an endoscopic insertion member, providing an endoscopic retractor instrument including a balloon, and securing the retractor instrument to a distal end portion of the insertion member so that the balloon is disposed in a collapsed configuration along an outer surface of the insertion member. Further steps of the method include inserting the distal end portion of the insertion member together with the collapsed balloon into a patient, and thereupon inflating the balloon to form an enlarged or expanded configuration extending at least partially in a distal direction away from the distal end portion of the insertion member. The enlarged or expanded configuration of the balloon is used to spread internal tissues of the patient in a region located distally of the insertion member.

Where the balloon has an expandable or inflatable end portion and at least one expandable or inflatable spacer portion connecting the end portion to the endoscopic insertion member, the inflating of the balloon includes inflating the spacer portion to separate the end portion from the endoscopic insertion member and inflating the end portion to engage the tissues.

Where the enlarged or expanded configuration of the balloon defines at least one opening, the method further comprises directly accessing the tissues from the distal end portion of the insertion member via the opening.

The securing of the balloon to the insertion member preferably includes attaching a sheath and an end cap to the insertion member, the balloon being attached to at least one of the sheath and the end cap. The sheath is preferably attached to the insertion member by adhesively coupling the sheath to the insertion member. At least one protective strip is removed from an adhesive region on the sheath and then the exposed adhesive region is placed into contact with an outer surface of the sheath or the endoscope insertion member and pressed against the insertion member to form an adhesive bond.

At the termination of the procedure, the insertion member is removed from the patient, together with the sheath and the balloon. Then a tear string is pulled along at least a portion of the sheath to sever the sheath, which is subsequently separated from the insertion member.

An endoscopic retractor instrument comprises a plurality of parts movably connected to one another, means for disposing the parts in a collapsed or reduced-size configuration at a distal end portion of an insertion member of an endoscope, and an actuator such as a pressurization tube operatively connected to the parts for enabling a movement of the parts relative to one another so that the parts assume an enlarged or expanded configuration extending at least partially in a distal direction away from the distal end portion of the insertion member for spreading internal tissues of a patient- to facilitate access to the tissues via the insertion member. The means for disposing the parts preferably includes means such as an endoscope sheath and an endoscope end cap for removably attaching the parts to an outer surface of the insertion member.

The parts preferably include a plurality of expandable or inflatable balloon parts that are differently shaped parts of a single tubular balloon member. The balloon member is preformed to assume an expanded configuration having the differently shaped parts.

Pursuant to a particular embodiment of the method, the inflating of the balloon or bladder includes expanding the end portions so that one or both assumes the form of a coil, the spacer portion being one of a plurality of elongate expandable or inflatable spacer parts each having one end connected to and communicating with one of the end portions and an opposite end connected to and communicating with another one of the end portions. More generally stated, the enlarged or expanded configuration of the balloon or bladder may be at least partially a spiral configuration, the inflating of the balloon or bladder including the forming of the balloon or bladder at least partially into the spiral configuration.

In this method, the securing of the balloon or bladder to the insertion member may include attaching a sheath and an end cap to the insertion member, the balloon or bladder being attached to at least one of the sheath and the end cap.

As discussed above, the retractor balloon is preferably manufactured from a single elongate preform which is differentially bent and provided with a "memory" to form the end portions and spacer portions.

A sheath used to attach a balloon-type retractor to an endoscopic insertion member may take the form of a web or sheet, which is wrapped about at least a distal end portion of the insertion member, adhesively fastened about the insertion member, and inserted with the insertion member into a patient. Subsequently the insertion member with the sheath wrapped thereabout is removed from the patient. If a tear string is embedded in the sheath, the tear string is pulled to sever the sheath along a predetermined line where the sheath is weakened, e.g., via a score line or a reduced thickness. Subsequently the insertion member and the torn or severed sheath are separated from one another.

The wrapping of the sheath preferably includes providing a cradle member having a groove, placing the web or sheet over the cradle member so that a portion of the web or sheet lies in the groove, disposing the endoscopic insertion member on the portion of the web or sheet lying in the groove, and winding a side portion of the web or sheet about the endoscopic insertion member after the disposing thereof on the web or sheet. This technique facilitates application of the sheath in that the endoscopic insertion member is partially surrounded by the sheath in the cradle member and the operator or user need only fold the longitudinal edge portions over one another and press the adhesive regions to effectuate an effectively secure closure.

The fastening of the sheath to the endoscopic insertion member preferably includes adhesively securing a first longitudinal edge region of the web or sheet to an outer surface of the endoscopic insertion member, and subsequently adhesively securing a second longitudinal edge region of the web or sheet to on outer surface of the web or sheet.

As discussed above, an endoscopic retractor in the shape of a balloon may be attached in a collapsed configuration to the insertion member along an outer side thereof via either the sheath or an end cap or both. After the inserting of the insertion member and the sheath into the patient, the balloon is inflated to assume an enlarged or expanded configuration extending at least partially in a distal direction away from the insertion member. The enlarged or expanded configuration of the balloon is used to spread internal tissues of the patient to facilitate at least a visual access to the tissues. This operation is typically done during a withdrawal of the endoscopic insertion member from the patient.

Naturally, a retractor balloon or bladder in accordance with the invention expands radially or transversely, as well as longitudinally or axially. The transverse expansion of the instrument enables the application of pressure to the colon wall or other portion of a digestive tract or internal body tissues to separate the tissues and smooth out folds. This facilitates inspection and the performance of endoscopic operations on target tissues inside the patient.

The inflation element of a retractor instrument assembly in accordance with the present invention may include a feed tube or conduit connected to the balloon or bladder for enabling the delivery of a pressurizing fluid such as saline solution or a gas (air) to the balloon or bladder. This inflation tube is typically a flexible line extending back along an endoscopic insertion member to a pressurization device (e.g., a syringe) outside of the patient. The inflation tube may extend through the biopsy channel of an endoscope or, where a sheath is provided as discussed above, may extend through, or be incorporated as, a channel in the sheath.

The inflation element of a balloon-type retractor instrument assembly may include a one-way valve disposed between the inflation tube and the balloon or bladder. The valve automatically prevents the escape of the pressurizing fluid from the balloon or bladder and thus facilitates the use of the instrument in an endoscopic procedure. The valve may be disposed inside the balloon or bladder or alternatively in a nipple or nub element connected thereto. Where the inflation tube extends through a biopsy channel in an endoscope insertion member or endoscope sheath, the tube may be removably connected to the balloon or nipple, for instance, via a screw connection or a frangible link. The extraction of the inflation tube upon the disconnection thereof from the balloon clears the site of interest and thereby facilitates the performance of additional diagnostic or therapeutic procedures via the biopsy channel. This removal is not necessary where a sheath having multiple channels is used.

The present invention enables the insertion of a retractor deep inside a patient through a natural body opening. At the site of interest, whether a diagnostic or surgical site, the retractor is expanded to a configuration many times larger than the collapsed insertion configuration, thereby enabling a substantial spreading of internal tissues.

In a balloon-type retractor as disclosed herein, windows or openings are provided which allow direct access to the internal tissues of the patient from the distal end of an endoscopic insertion member. Upon expansion, the retractor provides transverse pressure on the wall of the gastrointestinal tract and expands the organ and smoothens the folds, allowing for the viewing and potential diagnostic and/or interventional activity. The windows or openings defined by the expanded retractor allow for an instrument such as a snare cautery device to capture a polyp. The openings are not so large, however, that the retraction process is impaired.

The inner diameter of a retractor pursuant to the present invention is preferably large enough to allow the operator to comfortably operate on a polyp or other lesion. The outer diameter of the device is sized correctly to support the colon walls in an open position but is not so large as to cause colonic perforation. The balloon diameter is large enough to allow support of the colon wall, but small enough as to not obstruct the visibility of the colon being retracted.

A retractor balloon as disclosed herein is made of a rubber or elastic polymeric material with limited expandability so that it will not be overextended, and burst. The collapsed configuration of the device after its use is flexible enough to permit extraction of the device from the colon or other hollow organ or reintroduction of the device into a sheath with which it was introduced.

Where a retractor balloon is attached to the distal end of an endoscope, as discussed above, the proximal end of the balloon may be configured to fit snugly, or with a clamping or securing attachment, over the outside of the distal end of the endoscope in a deflated configuration. The distal end of the balloon is configured so as not to interfere with insertion of the endoscope or visualization through the endoscope. Thus, the collapsed balloon is situated outside the field of visualization surrounding the endoscope lens, either in the same transverse plane as the lens or proximal to it. The endoscope with the attached retractor in a collapsed configuration is inserted into a hollow organ, e.g., the colon, to the most proximal end (farthest inside the patient) of the hollow organ as determined by the endoscopist. The balloon is then inflated using the inflation element at the proximal end of the insertion tubing. The distal portion of the balloon unfolds during this process and moves distal to the distal end of the endoscope, the proximal portion of the balloon inflates around the endoscope and may further secure the device to the endoscope. The spacer members secure the two balloon ends at a predetermined distance from one another. The endoscopist then slowly retracts the endoscope with the enlarged or expanded retractor and views the GI tract between the two ends of the retractor as the retractor places pressure on and expands or stretches the wall of the GI tract, minimizing tissue folds that can interfere with viewing of the organ. The spacing (windows, openings) between the ends of the balloon allow for diagnostic and interventional procedures by the endoscopist. In other words, as the endoscope is pulled back, the physician performs his or her examination, and the colon collapses behind the enlarged or expanded retractor, which provides a telescoped part of the colon in front of (distal to) the lens that is now distended to its full inner diameter, allowing for visualization of polyps or other pathology behind every fold and 360 degrees around the wall of the colon. When a polyp happens to come into view, the withdrawal procedure is interrupted, the telescope (retractor) is situated framing the polyp, and removal of the polyp takes place. Then, the polyp is captured and with the retractor still in place the withdrawal continues and the rest of the colon or other hollow organ is visualized.

Where a sheath is used as an attachment device for an endoscopic retractor, in accordance with the invention, the sheath provides the additional benefit of keeping the endoscope relatively free from contact with the patient's body fluids or fecal material. The sheath is made of a thin flexible material that is split from its proximal end to the distal end or to a point close to the distal end. One side of the split line has a permanent adhesive component that sufficiently overlaps the other side of the sheath to enable fixation of the sheath to an endoscope insertion member. The adhesive can be covered by a removable protective strip that is simply peeled off to expose the adhesive layer. The sheath is then wrapped over the endoscope and adhered to the non-adhesive side of the sheath, making a secure and fluid tight bond the entire length of the sheath. In order to easily apply a long and narrow sheath in accordance with the invention to an endoscope, the non-adhesive part of the sheath is first lightly bonded to the insertion shaft of the endoscope by means of a light-adhesive region also covered by a removable protective strip. Only once the first side is lightly bonded to the endoscope is the strip overlying the permanent glue remove. That side is then folded over the first side and permanently attached as described above. The sheath also contains an embedded tear-strip with a small portion of the tear-strip exposed, e.g., at the proximal end of the sheath, so as to facilitate grabbing of the tear strip and pulling it lengthwise down the sheath causing the sheath to easily split and be safely, cleanly and easily removed from the endoscope.

The distal end of the sheath is provided or associated with an end cap in the shape of a short tube that incorporates a transparent end portion that fits over the distal end of the endoscope insertion shaft, allowing for use of the endoscope's visualization capabilities and potentially the working channels of the endoscope.

A retractor balloon as discussed above may be permanently attached to the sheath, or may be separate from the sheath and attached to it only prior to an endoscopic procedure. Thus the sheath would be attached first to enclose the shaft of the endoscope, and then the retractor is placed upon the distal part of the sheath substantially proximal to the lens as not to interfere with visualization. The attachment can be by glue or other means.

The sheath may include built-in or insertable biopsy, suction and irrigation channels or any combination thereof or may include space along the length of the sheath to allow addition of said channels which may be comprised of substantially similar tubing as the insertion tubing of the aforementioned devices.

BRIEF DESCRIPTION OF THE DRAWINGS

FIGS. 4A–4D are schematic isometric views of an endoscopic insertion shaft and the sheath assembly of FIG. 3, showing successive steps in the application of the sheath assembly to the endoscope insertion shaft.

FIG. 5 is a detail schematic isometric view of a portion V of the sheath of FIG. 4A, on a larger scale.

FIG. 6 is a schematic isometric view of a support for an endoscope insertion member, to aid in the application process of FIGS. 4A–4D.

DETAILED DESCRIPTION OF THE PREFERRED EMBODIMENTS

Figure 1A:
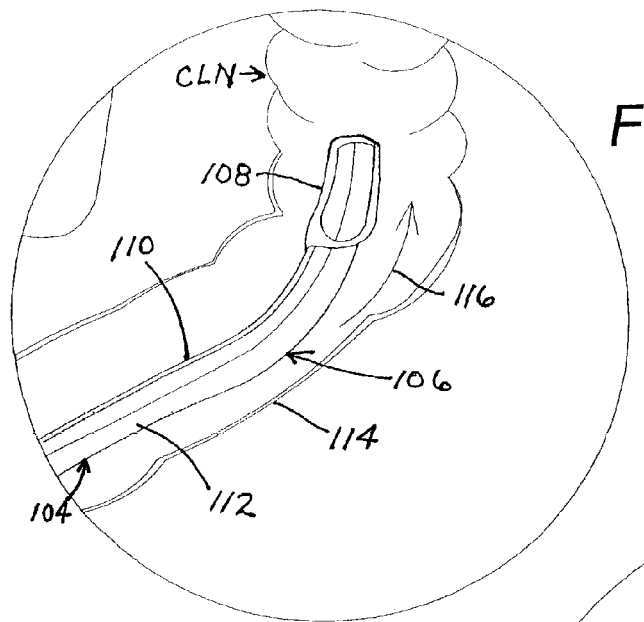
FIGS. 1A–1H are schematic cross-sectional views of a human colon, showing successive steps in the performance of an endoscopic polypectomy using an endoscopic insertion shaft provided at a distal end with a balloon-type endoscopic, in accordance with the present invention.

FIG. 1A shows an endoscope insertion member or shaft 104 encased in a sheath assembly 106 that carries, at a distal end, a balloon-type retractor 108 in a collapsed configuration. Retractor balloon 108 is essentially identical to that disclosed above with reference to FIGS. 1 and 2 and is connected to an inflation tube 110 extending longitudinally back along endoscope insertion member 104. Tube 110 may be a part of or connected to a sheath 112 of assembly 106. Alternatively, tube 110 may extend separately alongside sheath 112 and endoscope insertion member 104. In another alternative, tube 110 extends through a biopsy channel of endoscope insertion member 104.

It is to be noted that retractor balloon 108 is configured in its collapsed insertion configuration so as not to interfere with insertion of the endoscope member 104 or visualization through the endoscope. Thus, the collapsed retractor balloon 108 is situated outside the visual field of the endoscope lens (not shown), and is disposed either in the same transverse plane as the lens or proximal to it.

Figure 1B:
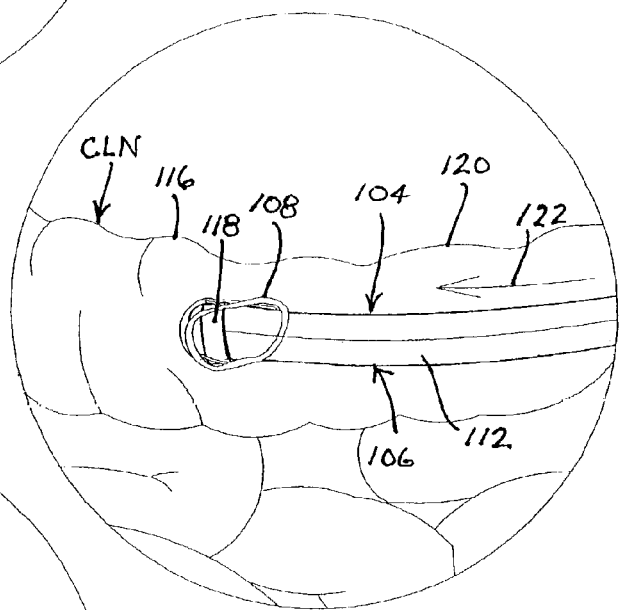
Figure 1C:
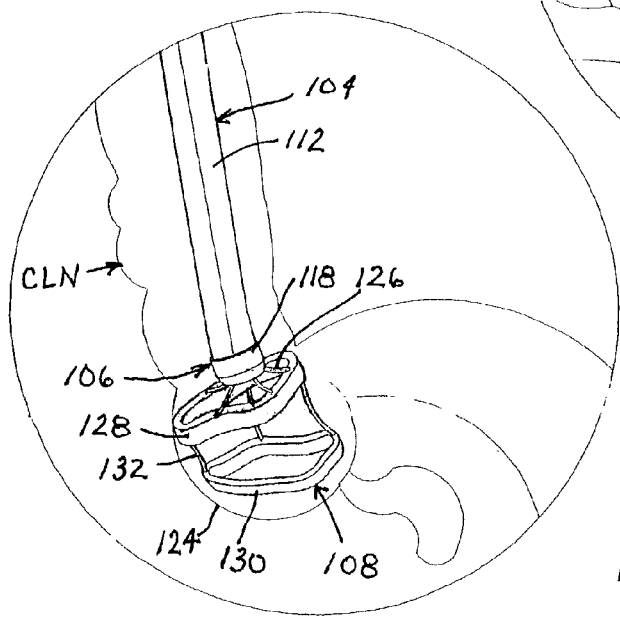
Figure 8:
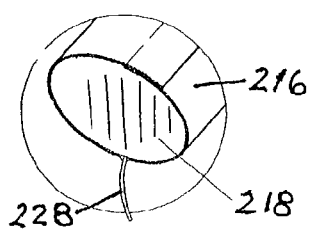
FIG. 8 is a detail view, on a larger scale, of a distal end of the sheath assembly of FIG. 7.

In the collapsed configuration, retractor balloon 108 is inserted together with a distal end portion of insertion member 104 into a hollow organ such as a colon CLN, as illustrated in FIG. 1A. FIG. 1A depicts the distal end portion of insertion member 104, sheath 112, and retractor balloon 108 being pushed through an ascending segment 114 of colon CLN, as indicated by an arrow 116. As shown in FIG. 1B, sheath assembly 106 includes an end cap 118 in addition to sheath 112. FIG. 1B shows insertion member 104, sheath assembly 106, and retractor balloon 108 moving along a horizontal segment 120 of the colon CLN (arrow 122). In FIG. 1C, the distal end portion of the endoscope insertion member 104 has reached the upstream terminus 124 of the colon CLN. At this juncture, a pressurizing fluid such as a saline solution is fed through tube 110 (FIG. 1A) to inflate retractor balloon 108 from the collapsed insertion configuration of FIGS. 1A and 8B. During the inflation process, the distal portion of retractor balloon 108 unfolds and moves distal to the distal end of the endoscope insertion member 104. The proximal portion of the retractor balloon 108 may be designed to inflate around the endoscope to further secure the retractor balloon to the endoscope.

FIG. 1C shows retractor balloon 108 in a partially enlarged or expanded configuration. Tubules 126, which communicate with tube 110, extend from sheath end cap 118 to a proximal toroidal end portion 128 of retractor balloon 108. End portion 128 is connected to a distal toroidal end portion 130 via a plurality of elongate axially extending spacer tubes 132. The spacer tubes 132 secure the two balloon end portions 128 and 130 at a predetermined distance from one another. Pressurizing fluid is conveyed through tubules 126, end portion 128, and tubes 132 to end portion 130.

Figures 1D, 1E:
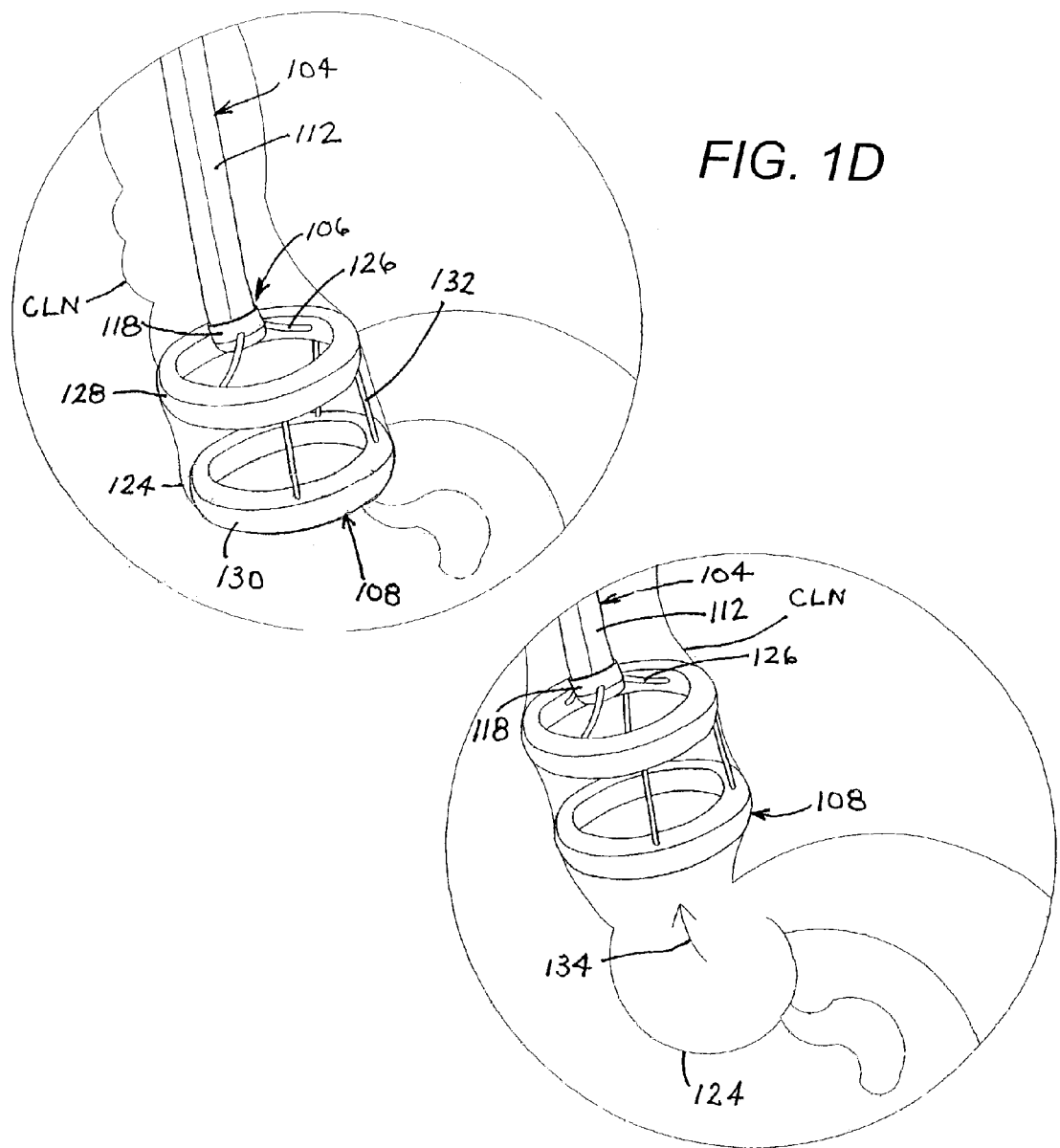
Figure 1F:
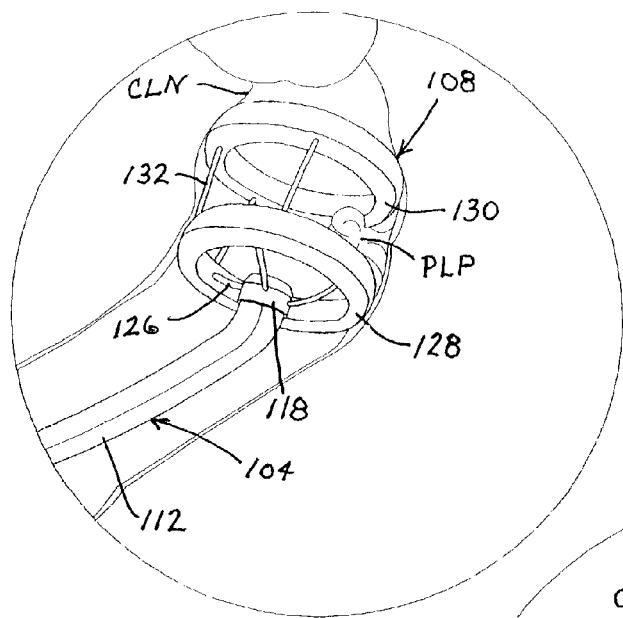

Once retractor balloon 108 has been inflated to a fully expanded configuration shown in FIG. 1D, the endoscope insertion member 104 is slowly pulled in a proximal direction out of the patient, as indicated by an arrow 134. During the withdrawal, the endoscopist views the wall of colon CLN through a window or opening (not separately labeled) defined by end portions 128 and 130 of retractor balloon 108. As it is pulled through colon CLN, the inflated retractor balloon 108 places pressure on and expands or stretches the wall of the colon, reducing or eliminating tissue folds that can interfere with viewing of the organ. The spacing (windows, openings) between end portions 128 and 130 allow for diagnostic and interventional procedures by the endoscopist. When a polyp PLP happens to come into view (FIG. 1F), the withdrawal procedure is interrupted with the retractor balloon 108 framing the polyp. Removal of the polyp PLP can then bee effectuated via a cauterization snare operation (not shown). The polyp PLP is captured and with the retractor 108 still in place the withdrawal may continue so that the remaining segment of the colon CLN or other hollow organ may be visualized.

Figure 1G:
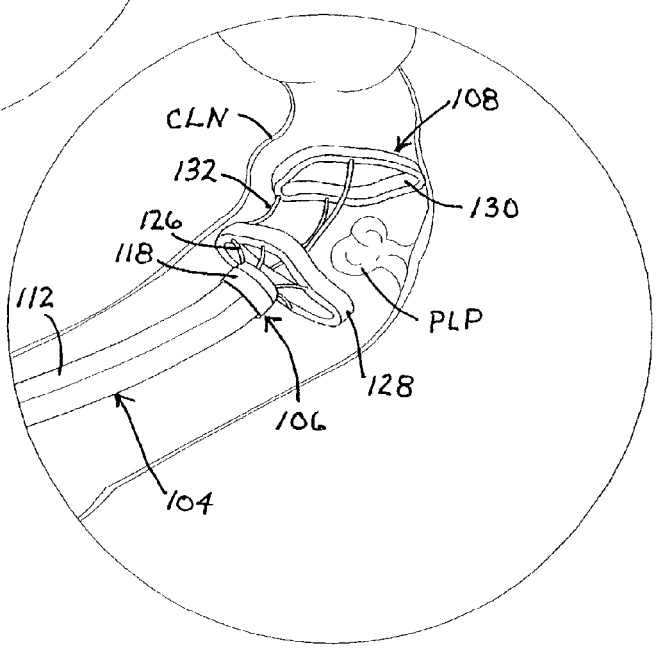
Figure 1H:
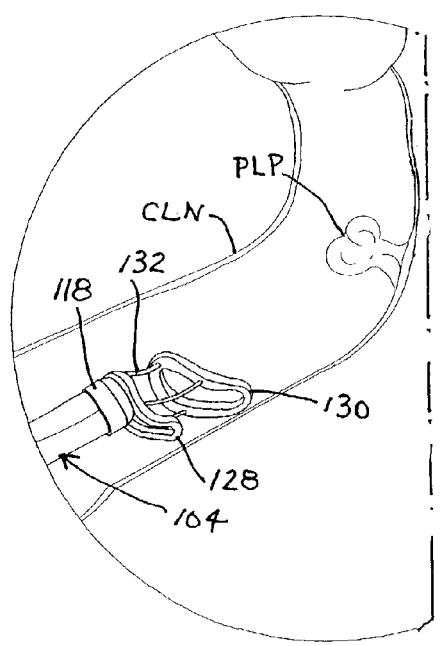

FIG. 1G depicts retractor balloon 108 in a state of partial deflation after an investigation has been completed. FIG. 1H depicts retractor balloon 108 in a state of mostly completed deflation during a withdrawal of endoscope insertion member 104. As discussed above with reference to FIGS. 1 and 2, an endoscopic scalpel or other sharp instrument may be inserted through the biopsy channel of the endoscope insertion member 104 and used to perforate the retractor balloon, thereby allowing depressurization thereof. Alternatively, if the retractor balloon communicates with tube 110 via a two-way valve, then depressurization may be accomplished by applying suction from the proximal end of the tube. In that case, tube 110 must have a transverse rigidity preventing collapse thereof in the presence of suction forces.

Figure 2A:
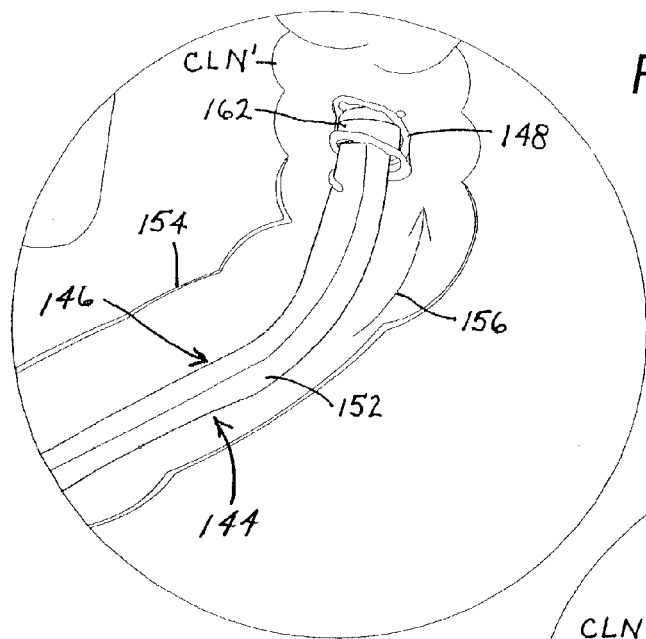
FIGS. 2A–2H are schematic cross-sectional views similar to FIGS. 1A–1H, showing successive steps in the performance of an endoscopic polypectomy using an endoscopic insertion shaft provided at a distal end with an alternative balloon-type endoscopic retractor, in accordance with the present invention.

FIG. 2A shows an endoscope insertion member or shaft 144 encased in a sheath assembly 146 that carries, at a distal end, a balloon-type retractor 148 in a collapsed configuration. Retractor balloon 148, at least in an expanded configuration (FIGS. 2D, 9E), takes the form of a spiral or helix. Retractor balloon 148 is connected to an inflation tube (not shown) extending longitudinally back along endoscope insertion member 144. As discussed above with reference to FIG. 1A, that tube may be a part of or connected to a sheath 152 of assembly 146. Alternatively, the inflation tube may extend separately alongside sheath 152 and endoscope insertion member 144. In another alternative, the inflation tube extends through a biopsy channel of endoscope insertion member 144.

It is to be noted that retractor balloon 148 is configured in its collapsed insertion configuration so as not to interfere with insertion of the endoscope member 144 or visualization through the endoscope. Thus, the collapsed retractor balloon 148 is situated outside the visual field of the endoscope lens (not shown), and is disposed either in the same transverse plane as the lens or proximal to it.

In the collapsed configuration, retractor balloon 148 is inserted together with a distal end portion of insertion member 144 into a hollow organ such as a colon CLN', as illustrated in FIG. 2A. The distal end portion of insertion member 144, together with sheath 152 and retractor balloon 148 are pushed first through an ascending segment 154 of colon CLN', as indicated by an arrow 156, and then through a horizontal segment 158, as indicated by an arrow 160 in FIG. 2B.

Figure 2B:
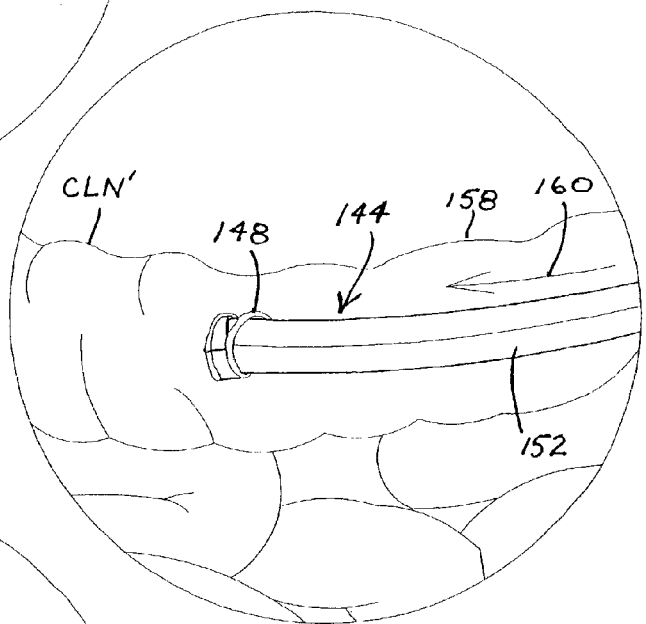
Figure 2C:
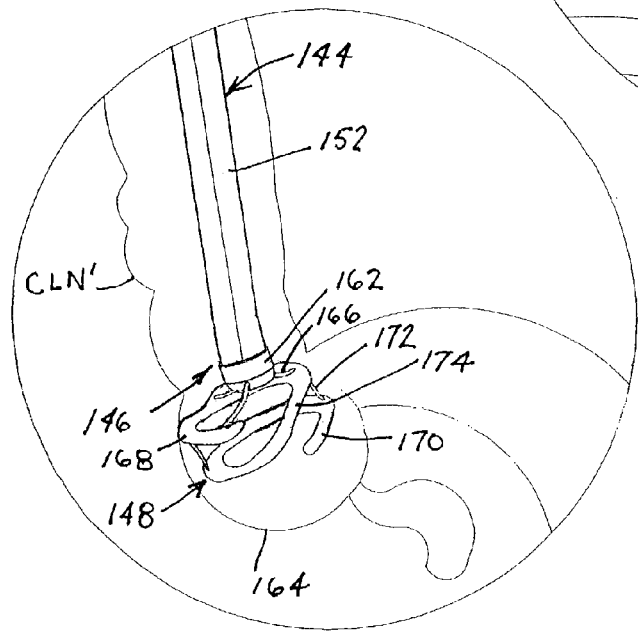

Sheath assembly 146 includes an end cap 162 in addition to sheath 152, as shown in FIGS. 2B and 2C. Once the distal tip of the endoscope insertion member 144 has reached a beginning terminus 164 of the colon CLN', as shown in FIG. 2C, a pressurizing fluid such as a saline solution is fed to retractor balloon 148 to expand the same from the collapsed insertion configuration of FIGS. 2A and 2B. During the inflation process, a distal portion of retractor balloon 148 unfolds and moves distal to the distal end of the endoscope insertion member 144, as shown in FIG. 2C. A proximal portion of the retractor balloon 148 may be designed to inflate around the endoscope to further secure the retractor balloon to the endoscope.

FIG. 2C shows retractor balloon 148 in a partially enlarged or expanded configuration. Tubules 166, which communicate at one side with the inflation tube, extend from sheath end cap 162 to a proximal end portion 168 of retractor balloon 148. End portion 168 communicates with a distal end portion 170 via a spiral central portion 172 and via a plurality of elongate axially extending spacer tubes 174. The spacer tubes 174 serve in part to secure the two balloon end portions 168 and 170 at a predetermined distance from one another. Pressurizing fluid is conveyed through tubules 166, end portion 168, and tubes 174 to end portion 170.

Figure 2D:
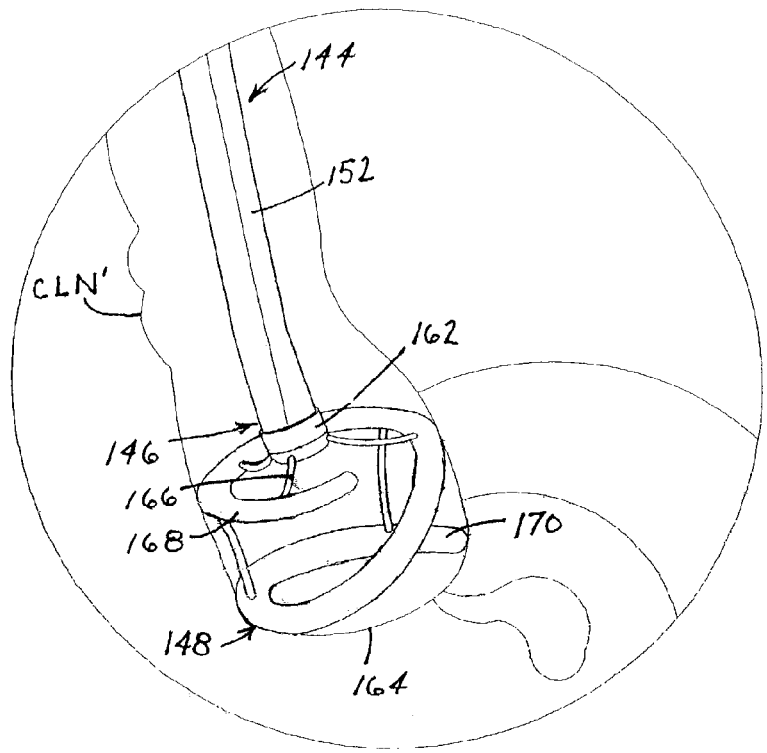
Figure 2E:
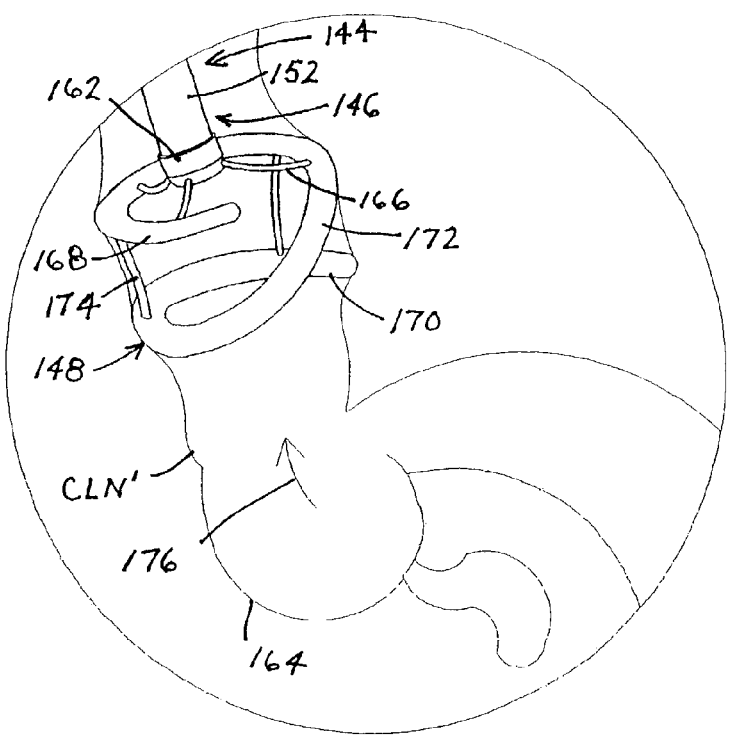
Figure 2F:
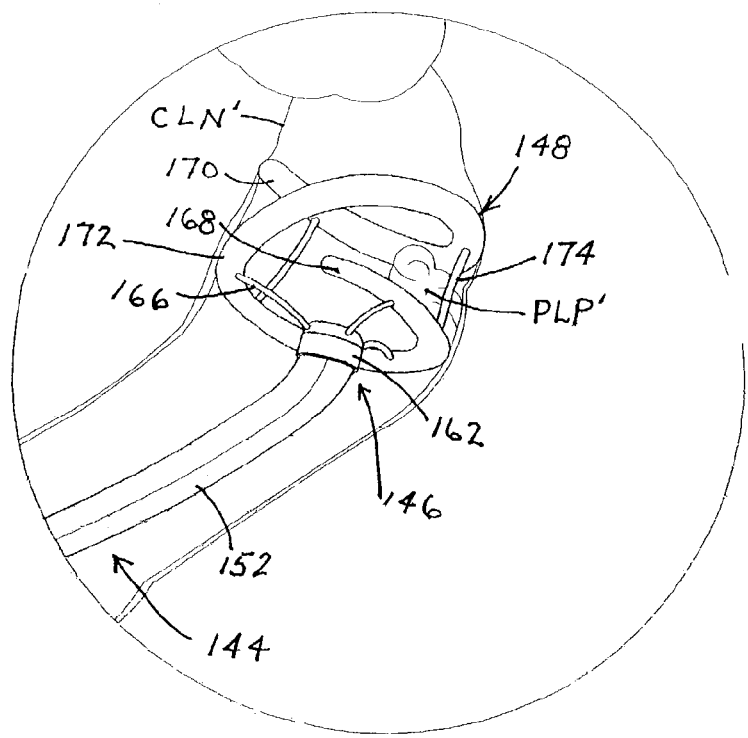

Once retractor balloon 148 has been inflated to a fully expanded configuration shown in FIG. 2D, the endoscope insertion member 144 is slowly pulled in a proximal direction out of the patient, as indicated by an arrow 176 (FIG. 2E). During the withdrawal, the endoscopist views the wall of colon CLN' through a window or opening (not separately labeled) defined by end portions 168 and 170 of retractor balloon 148. As it is pulled through colon CLN', the inflated retractor balloon 148 places pressure on and expands or stretches the wall of the colon, reducing or eliminating tissue folds that can interfere with viewing of the organ. The spacing (windows, openings) between end portions 168 and 170 allow for diagnostic and interventional procedures by the endoscopist. When a polyp PLP' happens to come into view (FIG. 2F), the withdrawal procedure is interrupted with the retractor balloon 148 framing the polyp. Removal of the polyp PLP can then bee effectuated via a cauterization snare operation (not shown). The polyp PLP' is captured and with the retractor 148 still in place the withdrawal may continue so that the remaining segment of the colon CLN' or other hollow organ may be visualized.

Figure 2G:
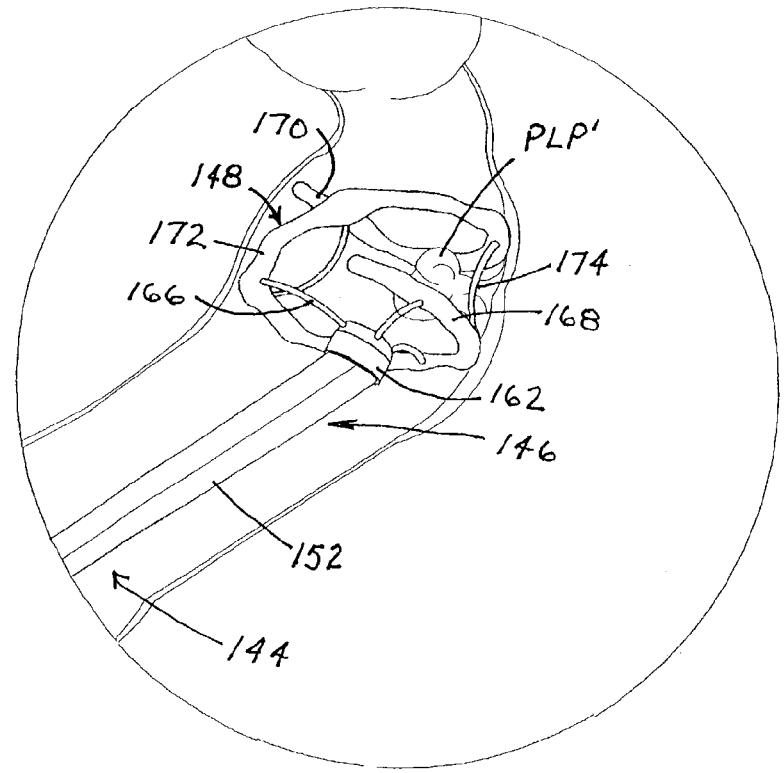
Figure 2H:
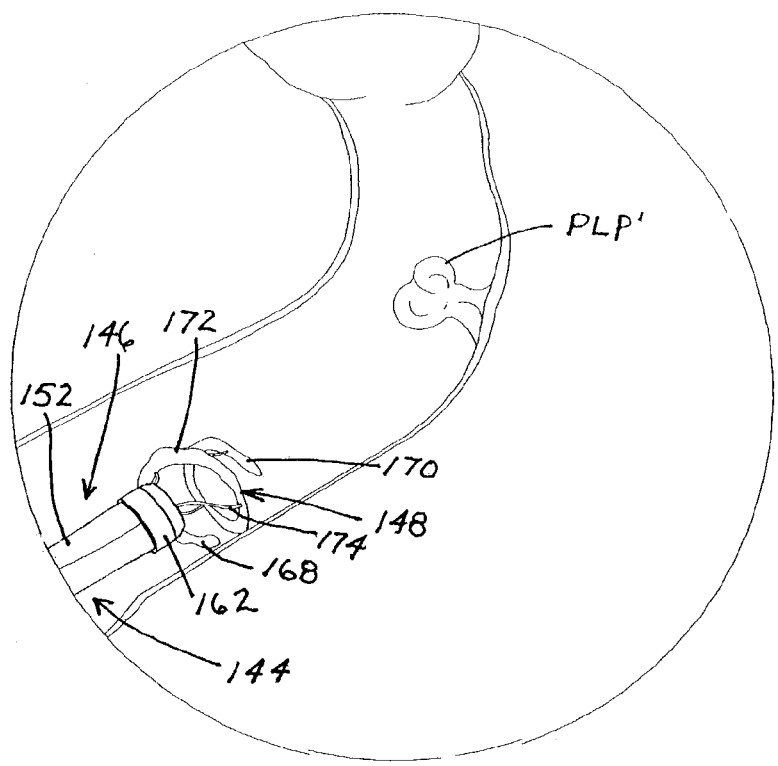

FIG. 2G depicts retractor balloon 148 in a state of partial deflation after an investigation has been completed. FIG. 2H depicts retractor balloon 148 in a state of mostly completed deflation during a withdrawal of endoscope insertion member 144. As discussed above with reference to FIGS. 1G and 1H, an endoscopic scalpel or other sharp instrument may be inserted through the biopsy channel of the endoscope insertion member 144 and used to perforate the retractor balloon, thereby allowing depressurization thereof. Alternatively, if the feed channel extending to tubules 166 is provided with a two-way valve and no one-way valve, then depressurization may be accomplished by applying suction from the proximal end of the tube.

Figure 3:
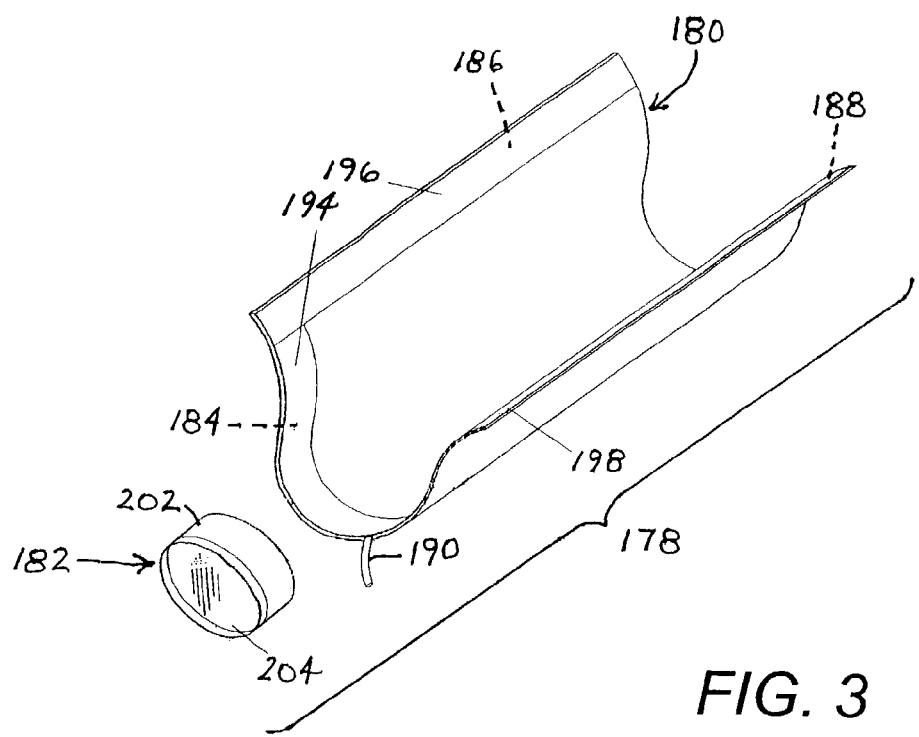
FIG. 3 is a schematic exploded isometric view of an endoscopic sheath assembly utilizable in the procedures of FIGS. 1A-1H and 2A-2H, in accordance with the present invention.

Sheath assembly 106 or 146 may take the form shown in FIG. 3 et seq. As depicted in FIG. 3, an endoscopic sheath assembly 178 includes an endoscope sheath 180 in the form of a web member or sheet and further includes an endoscope end cap 182. Sheath 180 is provided with a layer of adhesive material 184, 186, 188 along a forward end region, a first longitudinal edge region and a second longitudinal edge region, respectively (not separately enumerated). Sheath 180 is further provided along a weakened (e.g., thinned or scored) region (not separately labeled) with an embedded tensile member 190 such as a tear string for enabling a severing of the sheath in preparation for removal of the sheath from an endoscope insertion member 192 (FIG. 4A). Releasable protective cover strips 194, 196, 198 are removably attached to the adhesive layers or regions 184, 186, 188. Preferably, the adhesive material of layers or regions 184 and 186 is a permanent adhesive, while the adhesive material of layer or region 188 forms a separable or releasable bond.

In applying endoscopic sheath assembly 178 to endoscope insertion member 192 (FIG. 4A), end cap 182 is first placed over a distal tip 200 of the insertion member. End cap 182 includes a substantially rigid collar 202 and a transparent plate 204. End plate 204 transmits illumination into a patient from a light outlet 206 on endoscope tip 200. Returning light passes through plate 204 and impinges on a lens 208.

After the placement of end cap 182 over distal tip 200 of insertion member 192, protective cover strip 198 is peeled away from longitudinal adhesive layer 188. In addition, protective cover strip 194 (see FIG. 5) is removed from adhesive layer 184. Adhesive layer 188 is aligned longitudinally with endoscope insertion member 192 with the latter in a straight configuration, parallel to an axis thereof. Adhesive layer 188 is pressed against insertion member 192. Then the distal end of sheath or web member 180 is wrapped around collar 202, as shown in FIG. 4B, so that adhesive layer 184 permanently bonds to end cap 182. Prior to completing the wrapping of the distal end of sheath or web member 180 about collar 202, protective cover strip 196 is peeled away from longitudinal adhesive layer 186 (see FIG. 5). The uncovered layer 186 of permanent adhesive is then placed into an overlapping configuration with the sheath or web 180 and bonded thereto (FIG. 4C) so that the sheath surround the endoscope insertion member 192 in tight fluid-sealed fit (FIG. 4D).

An alternative method of applying sheath assembly 178 to endoscope insertion member 192 utilizes a support cradle 210 shown in FIG. 6. Support cradle 210 has a groove 212 of equivalent diameter to insertion member 192. First sheath or web member 180 with at least protective cover strip 194 removed is laid into groove 212. Endoscope insertion member 192 with end cap 182 positioned thereon is then placed atop sheath 180 so that collar 202 engages exposed adhesive layer 184. At this time, protective cover strip 198 may be removed to expose adhesive layer 188 which is then pressed along insertion member 192. Subsequently, strip 196 is removed to expose permanent-adhesive layer 186 which is then bonded to an outer surface of the sheath or web 180.

Figure 9:
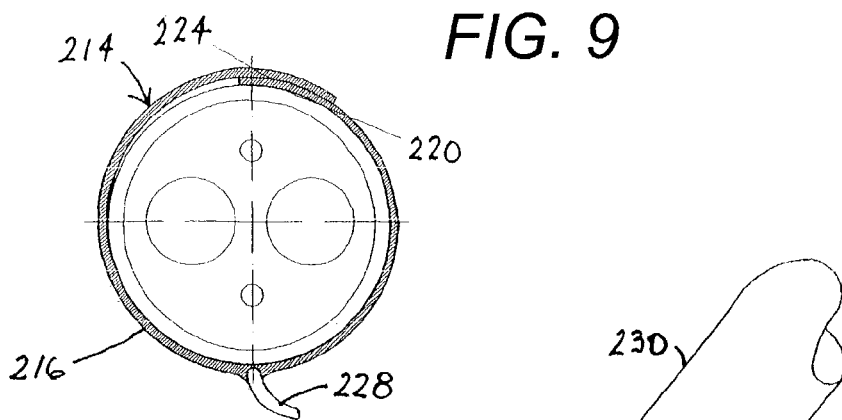
FIG. 9 is a schematic end elevational view, on an even larger scale, of the sheath assembly of FIG. 7.
Figure 7:
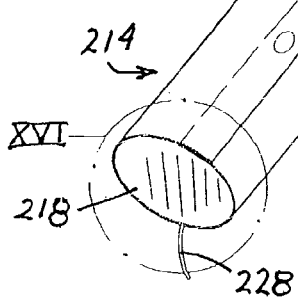
FIG. 7 is a schematic isometric view, of a modified endoscopic sheath assembly in accordance with the present invention, showing a step in the application of the sheath assembly to an endoscopic insertion shaft.

In an alternative sheath assembly 214 shown in FIG. 7, a sheath or web member 216 is attached to an end cap 218 during manufacture. Sheath or web 216 is provided along part of a first longitudinal edge with a layer 220 of lightly bonding adhesive covered by a releasable protective strip 222. Sheath or web 216 is provided along part of a second or opposing longitudinal edge with a layer 224 of permanently bonding adhesive covered by a releasable protective strip 226. A tear string 228 is embedded in sheath or web 216 and extends longitudinally therealong. Along a distal end portion of sheath assembly 214, the opposing longitudinal edge regions of the sheath or web 216 overlap and are bonded to one another, prior to introduction of an endoscope insertion member 230 into the sheath assembly, as shown in FIGS. 7 and 9.

Figure 10:
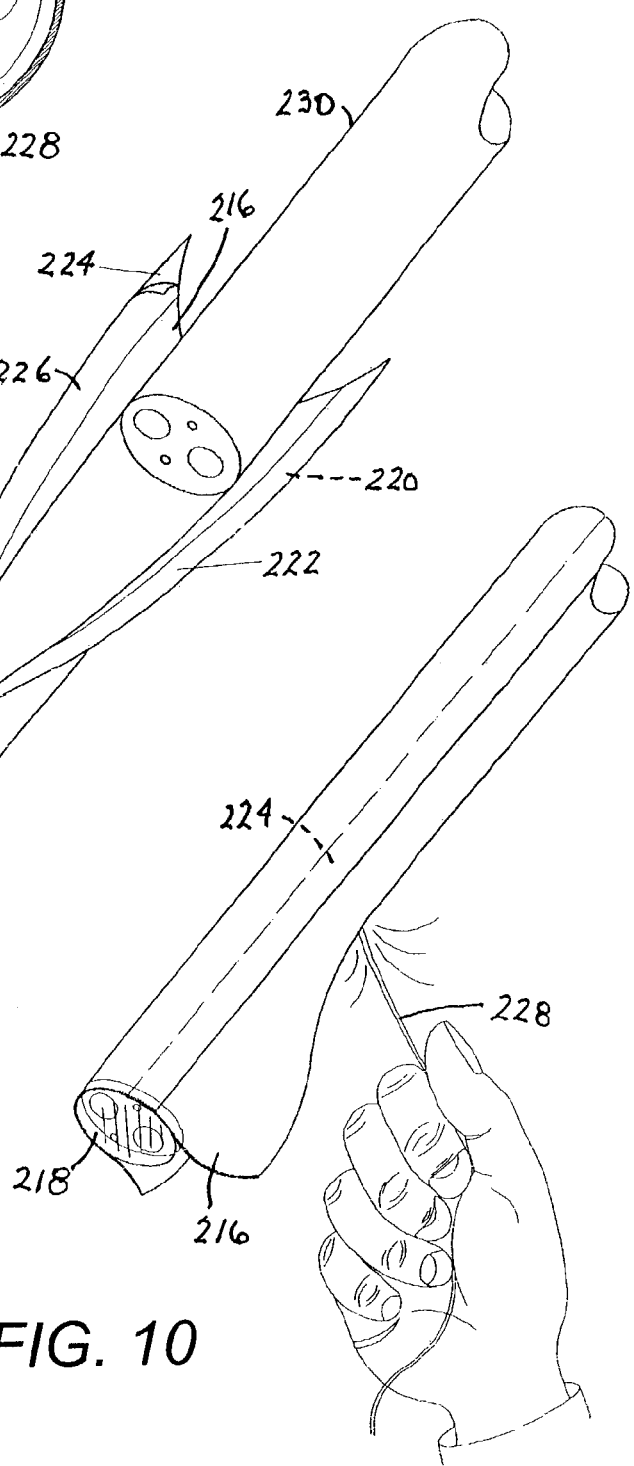
FIG. 10 is a schematic isometric view of a sheath assembly in accordance with the present invention on an endoscope insertion shaft, showing a stage in the removal of the sheath assembly from the endoscope insertion shaft.

FIG. 10 depicts an initial step in the removal of a sheath assembly 106, 146, 178, 214 from an endoscope insertion member (not separately labeled). A tear string 190, 228 is manually grasped and pulled to sever or rip the respective sheath 112, 152, 180, 216 along a straight or curved line extending at least a substantial portion of the length of the endoscope insertion member. The rip or tear in the sheath 112, 152, 180, 216 is preferably formed in a direction from the proximal end to the distal end of the instrument.

Figure 11A:
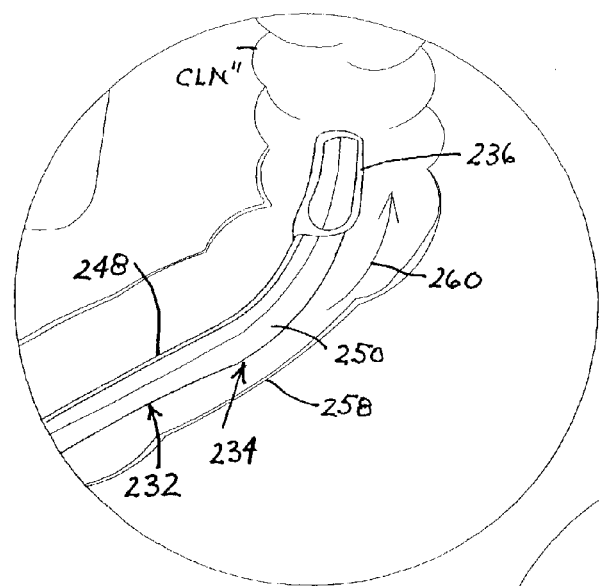
FIGS. 11A–11H are schematic cross-sectional views similar to FIGS. 1A–1H and 2A–2H, showing successive steps in the performance of an endoscopic polypectomy using an endoscopic insertion shaft provided at a distal end with another balloon-type endoscopic retractor, in accordance with the present invention.

FIG. 11A shows an endoscope insertion member or shaft 232 encased in a sheath assembly 234 that carries, at a distal end, a balloon-type retractor 236 in a collapsed configuration. Retractor balloon 236 is essentially a single tubular member that is preformed to assume a fully enlarged or expanded configuration in a tapered or frustoconical form as shown in FIGS. 11E and 11F. So configured, retractor balloon 236 has a C-shaped proximal end portion 238 that is bonded to sheath assembly 234 about a distal circumference thereof. Retractor balloon 236 further includes a coiled distal end portion 240 connected to C-shaped proximal end portion 236 via three circumferentially spaced struts or spacer members 242, 244, 246. The single tubular member that is the retractor balloon 236 has strut or spacer member 242 as an initial segment unitary or continuous at one end with the coiled distal end portion 240. Distal end portion 240, which has approximately one-and-half turns or windings (not separately designated), is in turn integral and continuous with strut or spacer member 244. At an end opposite coiled distal end portion 240, strut or spacer member 244 is unitary and continuous with one end of C-shaped proximal end portion 238. C-shaped proximal end portion 238 in turn leads directly into strut or spacer member 246, which is bonded, e.g., glued, to coiled distal end portion 240. Strut or spacer member 246 may be glued over an aperture (not shown) provided in coiled distal end portion 240. Similarly, strut or spacer member 242 is bonded to C-shaped proximal end portion 238 preferably over an aperture therein to facilitate the passage of pressurizing fluid to inflate retractor balloon from the collapsed insertion configuration of FIGS. 11A and 11B to the expanded use configuration of FIGS. 11D–11F.

Figure 11B:
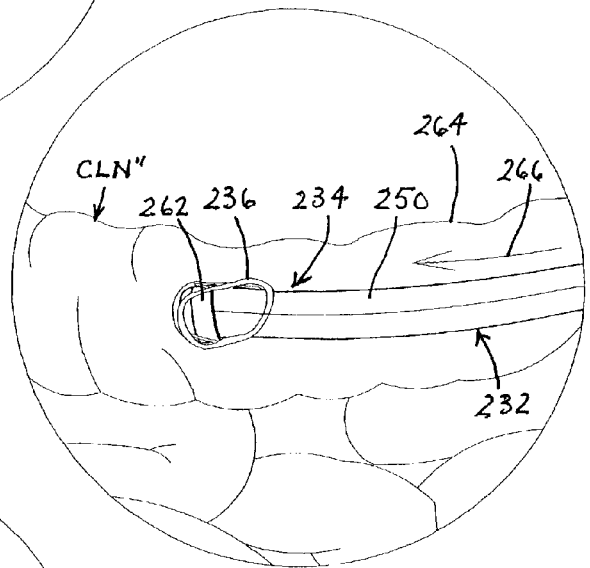
Figure 11C:
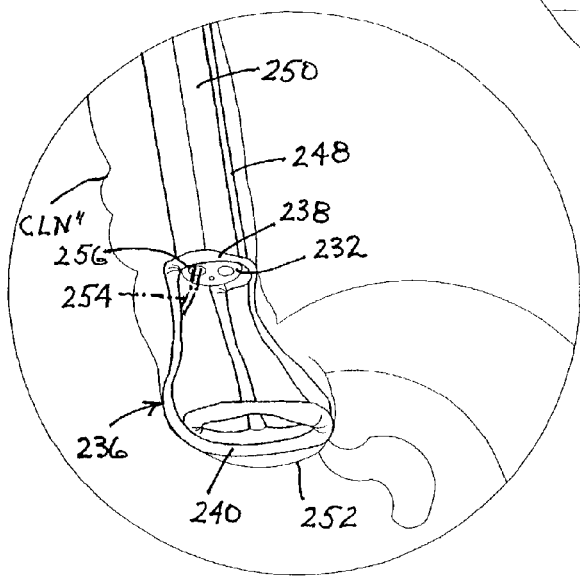

Retractor balloon 236 is expanded from the collapsed configuration of FIGS. 11A and 11B after the distal end of the endoscope insertion member 232 reaches the upstream end 252 of the colon shown in FIG. 11C. FIG. 11C shows retractor balloon 236 in partially expanded configuration. Retractor balloon 236 is expanded by means of an inflation or pressurization tube 248 (FIG. 11A) in the form of a catheter extending longitudinally back along endoscope insertion member 232. Tube 248 may be a part of or connected to a sheath 250 of assembly 234 or may extend loosely alongside sheath 250 and endoscope insertion member 232. Alternatively, an inflation tube 254 may extend through a biopsy channel 256 of endoscope insertion member 232. FIGS. 11D–11H show inflation tube 248 connected to an inlet end of spacer member 242 via a valve or port element 249. Preferably, tube 248 extends longitudinally along the endoscope insertion member 232 and is substantially collinear with spacer member 242. However, as illustrated in FIGS. 11D–11H, inflation tube 248 and spacer member 242 may be angularly offset about the endoscope insertion member 232.

It is to be noted that retractor balloon 236 is configured in its collapsed insertion configuration so as not to interfere with insertion of the endoscope member 232 or visualization through the endoscope. Thus, the collapsed retractor balloon 236 is situated outside the visual field of the endoscope lens (not shown), and is disposed either in the same transverse plane as the lens or proximal to it.

In the collapsed configuration, retractor balloon 236 is inserted together with a distal end portion of insertion member 232 into a hollow organ such as a colon CLN", as illustrated in FIG. 11A. FIG. 11A depicts the distal end portion of insertion member 232, sheath 250, and retractor balloon 236 being pushed through an ascending segment 258 of colon CLN, as indicated by an arrow 260. As shown in FIG. 11B, sheath assembly 234 may include an end cap 262 in addition to sheath 250. FIG. 11B shows insertion member 232, sheath assembly 234, and retractor balloon 236 moving along a horizontal segment 264 of the colon CLN" (arrow 266). In FIG. 11C, the distal end portion of the endoscope insertion member 232 has reached the upstream end 252 of the colon CLN". At this juncture, a pressurizing fluid such as a saline solution is fed through tube 248 (FIG. 11A) to inflate retractor balloon 236 from the collapsed insertion configuration of FIGS. 11A and 11B. During the inflation process, the coiled distal end portion 240 of retractor balloon 236 unfolds and moves distal to the distal end of the endoscope insertion member 232. The C-shaped proximal end portion 238 of the retractor balloon 236 inflates around the endoscope insertion member 232 to further secure the retractor balloon 236 to the endoscope.

Figure 11D:
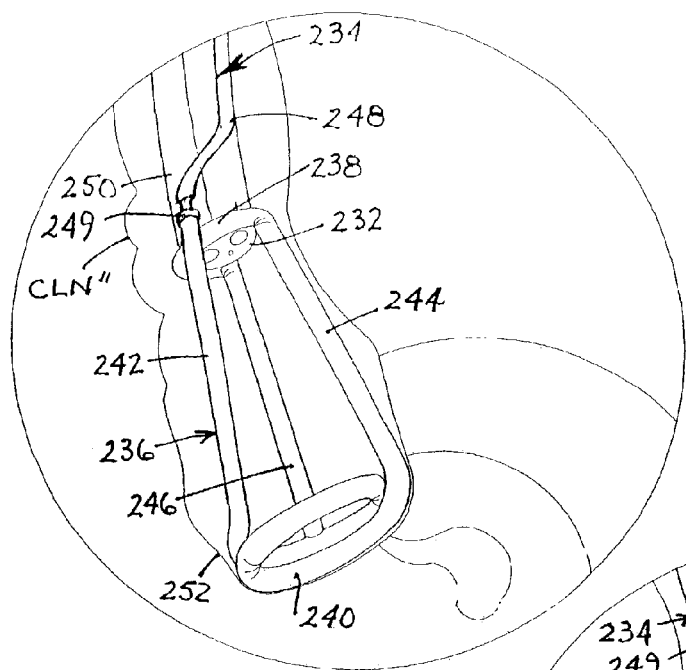
Figure 11E:
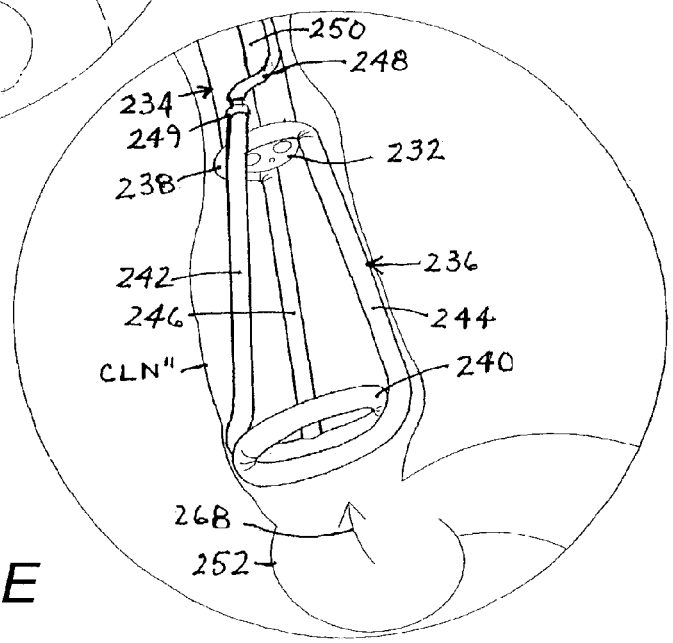
Figure 11F:
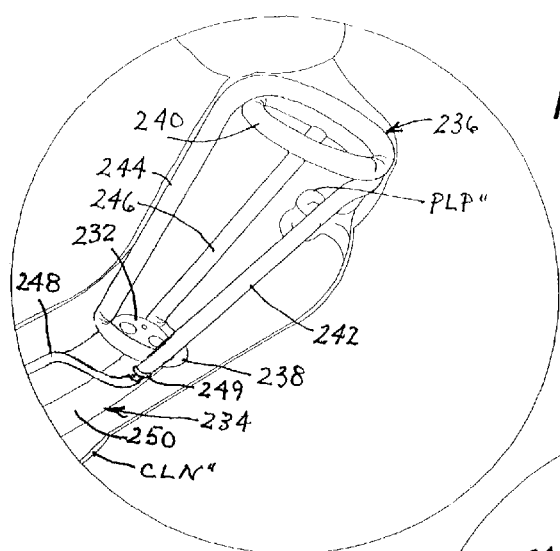

Once retractor balloon 236 has been inflated to a fully expanded configuration shown in FIG. 11D, the endoscope insertion member 232 is slowly pulled in a proximal direction out of the patient, as indicated by an arrow 268. During the withdrawal, the endoscopist views the wall of colon CLN" through three windows or openings defined on the near and far sides by proximal and distal end portions 238 and 240 and on the lateral sides by struts or spacer members 242, 244, 246. As it is pulled through colon CLN", the inflated retractor balloon 236 stretches the wall of colon CLN" facilitating a viewing of the organ by the endoscopist. The three windows or openings between end portions 128 and 130 and struts or spacer members 242, 244, 246, as well as the opening (not separately labeled) encircled by coiled distal end portion 240 permit diagnostic and interventional procedures via endoscope insertion ememeber 232. When a polyp PLP" happens to come into view (FIG. 11F), the withdrawal procedure is interrupted with the retractor balloon 236 framing the polyp. Removal and capture of the polyp PLP" can then be effectuated via a cauterization snare operation.

Figure 11G:
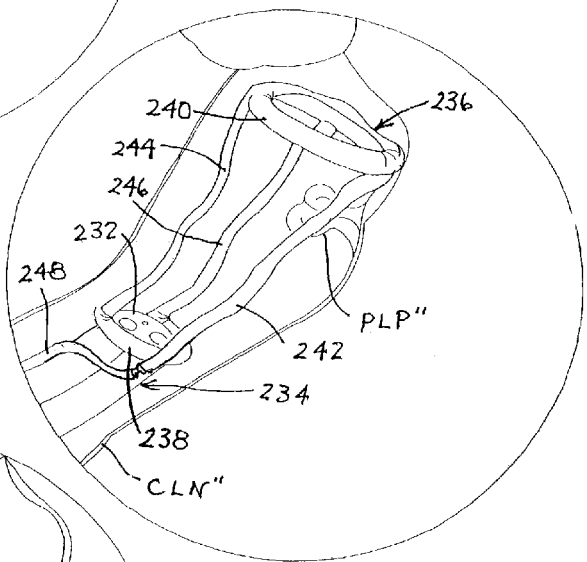
Figure 11H:
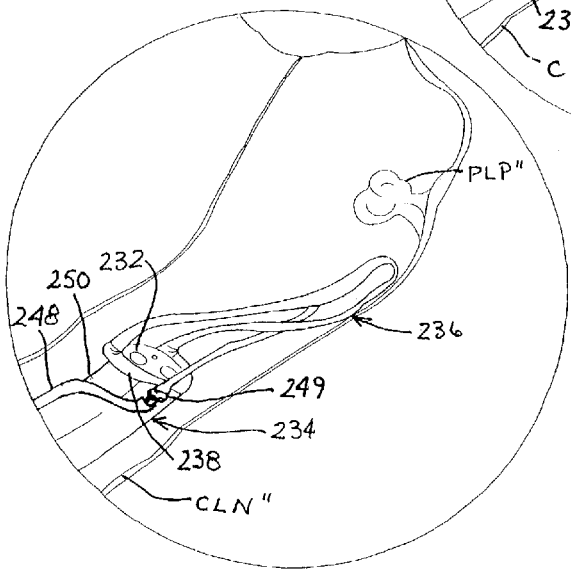

FIG. 11G depicts retractor balloon 236 in a state of partial collapse after an investigation or intervention has been completed. FIG. 11H depicts retractor balloon 236 in a state of essentially total collapse during a withdrawal of endoscope insertion member 232. As discussed above, an endoscopic scalpel or other sharp instrument may be inserted through the biopsy channel of the endoscope insertion member 232 and used to puncture retractor balloon 236, thereby allowing depressurization thereof. Alternatively, if retractor balloon 236 communicates with tube 248 via a two-way valve, then depressurization may be accomplished by applying suction from the proximal end of the tube. In that case, tube 248 must have a transverse rigidity preventing collapse thereof in the presence of internal suction forces.

Although the invention has been described in terms of particular embodiments and applications, one of ordinary skill in the art, in light of this teaching, can generate additional embodiments and modifications without departing from the spirit of or exceeding the scope of the claimed invention. Fasteners other than a sheath assembly may be provided for securing a balloon-type endoscopic retractor to the distal end of an endoscopic insertion member such as a flexible endoscope. Such fasteners include glue, clamps, elastic bands, and balloon elements, for instance in the shape of a C or an O. The fastener may be a separate element or incorporated into the balloon retractor as a part thereof.

It is to be noted that the retractor instrument and associated methodology disclosed herein may be used with laparoscopes and other rigid endoscopes, as well as with flexible endoscopes. Thus, the term "endoscope insertion shaft" or "endoscope insertion member" as used herein refers to any type of endoscope, whether flexible such as a colonoscope or rigid such as a laparoscope.

The word "endoscopic" as in the term "endoscopic insertion member" is used more broadly herein to denote any type of instrument part inserted into a patient in a minimally invasive surgical procedure involving a flexible or rigid endoscope. For example, an endoscopic insertion member may be a laparoscopic forceps insertable through a trocar sleeve or cannula into a patient for use in a laparoscopic procedure. A balloon retractor in accordance with the invention may be attached about the distal end of the forceps for spreading tissues to facilitate use of the forceps.

The word "spiral" or "spiraling" is used herein to denote a configuration of an elongate member wherein than member is wound about an axis. A coil is a spiral where successive turns are in close juxtaposition or adjacent to one another.

Accordingly, it is to be understood that the drawings and descriptions herein are proffered by way of example to facilitate comprehension of the invention and should not be construed to limit the scope thereof.

What is claimed is:

1. An endoscopic retractor instrument assembly comprising:
a balloon having at least one expandable or inflatable end portion and at least one expandable or inflatable spacer portion connected to said end portion, said balloon being a bent and wound elongate tubular form defining a singular flow path for the introduction of a pressurizing fluid;
a fastener component for securing said balloon to a distal end of an endoscopic insertion member, said balloon being disposed in a collapsed configuration along an outer surface of said endoscopic insertion member; and
an inflation element operatively coupled with said balloon for enabling an inflating of said balloon from said collapsed configuration to an expanded use configuration in which said spacer portion pushes said end portion at least partially in a distal direction away from said distal end of said endoscopic insertion member for spreading internal tissues of a patient to facilitate access to said tissues.

2. The retractor instrument assembly defined in claim 1 wherein said balloon is a unitary single-piece balloon preformed so that said expanded use configuration includes said end portion and said spacer portion.

3. The retractor instrument assembly defined in claim 1 wherein said fastener component includes an element taken from the group consisting of (a) a sheath disposable about the endoscopic insertion member and (b) an end cap attached over a distal tip of the endoscopic insertion member.

4. The retractor instrument assembly defined in claim 3 wherein said sheath includes at least one adhesive strip for detachably securing said sheath to said insertion member.

5. The retractor instrument assembly defined in claim 3 wherein said sheath includes a tear string for severing said sheath to facilitate removal thereof from said insertion member.

6. The sheath assembly defined in claim 5 wherein said tear string extends along a weakened region of said sheath.

7. The retractor instrument assembly defined in claim 1 wherein said end portion takes the form of a coil.

8. The retractor instrument assembly defined in claim 1 wherein said spacer portion is one of a plurality of spacer portions connecting said end portion to said endoscopic insertion member, said spacer portions extending substantially parallel to one another.

9. The retractor instrument assembly defined in claim 1 wherein said balloon includes another end portion having a C shape disposable about said endoscopic insertion member.

10. The retractor instrument assembly defined in claim 1 wherein said spacer portion is an elongate tube extending between and communicating with each of said end portions.

11. The retractor instrument assembly defined in claim 1 wherein said end portion is one of two tubular end portions and said spacer portion is one of three elongate tubular spacer portions, one of said end portions having a wound configuration including more than one coil, another of said end portions having a C-shaped configuration.

12. The retractor instrument assembly defined in claim 8 wherein said spacer portions are substantially linear segments of said balloon and extend substantially parallel to an axis of said balloon.

13. A medical method comprising:
providing a flexible endoscopic insertion member;
providing an endoscopic retractor instrument including a balloon;
securing said retractor instrument to a distal end portion of said insertion member so that said balloon is disposed in a collapsed configuration along an outer surface of said insertion member;
inserting said distal end portion of said insertion member together with the collapsed balloon into a digestive tract of a patient;
upon inserting of said distal end portion and said collapsed balloon into the digestive tract of the patient, inflating said balloon to form an enlarged or expanded configuration extending at least partially in a distal direction away from said distal end portion of said insertion member; and
using said enlarged or expanded configuration of said balloon to spread internal tissues of the digestive tract of the patient in a region located distally of said insertion member.

14. The method defined in claim 13 wherein said balloon has a pair of expandable or inflatable end portions and at least one expandable or inflatable spacer portion connecting said end portions to one another, the inflating of said balloon including inflating said spacer portion to separate said end portions from one another and inflating said end portions to engage said tissues.

15. The method defined in claim 14 wherein the inflating of said balloon includes expanding said end portions so that at least one of said end portions assumes the form of a coil, said spacer portion being one of a plurality of elongate expandable or inflatable spacer parts each having one end connected to and communicating with one of said end portions and an opposite end connected to and communicating with another an opposite one of said end portions.

16. The method defined in claim 13 wherein said enlarged or expanded configuration of said balloon defines at least one opening, further comprising directly accessing said tissues from said distal end portion of said insertion member via said opening.

17. The method defined in claim 13 wherein said balloon is a single elongate tubular member preformed to assume said enlarged or expanded configuration upon an expansion of said balloon, the inflating of said balloon including guiding an inflation fluid along a single path through said balloon.

18. The method defined in claim 13 wherein the enlarged or expanded configuration of said balloon is at least partially a spiral configuration, the inflating of said balloon including the forming of said balloon at least partially into said spiral configuration.

19. The method defined in claim 13 wherein the securing of said balloon to said insertion member includes attaching a sheath and an end cap to said insertion member, said balloon being attached to at least one of said sheath and said end cap.

20. The method defined in claim 19 wherein the attaching of said sheath to said insertion member includes adhesively coupling said sheath to said insertion member.

21. The method defined in claim 19, further comprising:
removing said insertion member from the patient, together with said sheath and said balloon;
after the removing of said insertion member, pulling a tear string along at least a portion of said sheath to sever said sheath; and
separating the severed sheath from said insertion member.

22. The method defined in claim 13 wherein the using of said enlarged or expanded configuration of said balloon to spread internal tissues of the patient includes withdrawing said endoscope insertion member from the patient while dragging said enlarged or expanded configuration of said balloon behind said endoscope insertion member.

23. The method defined in claim 14 wherein said spacer parts are substantially linear segments of said balloon and extend substantially parallel to an axis of said balloon.

24. An endoscopic retractor instrument comprising:
a plurality of parts movably connected to one another;
means for disposing said parts in a collapsed or reduced-size configuration at a distal end portion of an endoscopic insertion member; and
actuation means operatively connected to said parts for enabling a movement of said parts relative to one another so that said parts assume an enlarged or expanded configuration extending at least partially in a distal direction away from said distal end portion of said insertion member for spreading internal tissues of a patient to facilitate access to said tissues via said insertion member,
said means for disposing said parts including means for removably attaching said parts to an outer surface of said insertion member, said means for removably attaching including an attachment member taken from the group consisting of an endoscope sheath and an endoscope end cap, said parts being disposed at least partially along an outer surface of said attachment member.

25. The retractor instrument defined in claim 24 wherein said parts include a plurality of expandable or inflatable balloon parts.

26. The retractor instrument defined in claim 25 wherein said parts are differently shaped parts of a single tubular balloon member, said balloon member being preformed to assume an expanded configuration having said differently shaped parts.

27. The retractor instrument defined in claim 24 wherein said parts include at least one expandable or inflatable balloon part, said sheath having a channel, further comprising an inflation tube extending through said channel and operatively connected to said balloon part for expanding or inflating same.

* * * * *